(12) United States Patent
Bergstrom et al.

(10) Patent No.: US 10,571,441 B2
(45) Date of Patent: Feb. 25, 2020

(54) PISTON AND PROCESS COLUMN

(71) Applicant: GE Healthcare Bio-Sciences AB, Uppsala (SE)

(72) Inventors: Andreas Bergstrom, Uppsala (SE); Stefan Kjell Eriksson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 381 days.

(21) Appl. No.: 15/100,916

(22) PCT Filed: Dec. 8, 2014

(86) PCT No.: PCT/SE2014/051463
§ 371 (c)(1),
(2) Date: Jun. 1, 2016

(87) PCT Pub. No.: WO2015/088427
PCT Pub. Date: Jun. 18, 2015

(65) Prior Publication Data
US 2016/0305918 A1    Oct. 20, 2016

(30) Foreign Application Priority Data
Dec. 9, 2013    (SE) .................................... 1351465

(51) Int. Cl.
*B01D 15/18*    (2006.01)
*B01D 15/20*    (2006.01)
(Continued)

(52) U.S. Cl.
CPC .......... *G01N 30/606* (2013.01); *B01D 15/18* (2013.01); *B01D 15/206* (2013.01); *B01D 15/22* (2013.01);
(Continued)

(58) Field of Classification Search
CPC .. G01N 30/60; G01N 30/606; G01N 30/6021; G01N 30/6026; G01N 30/6017; G01N 30/6004; G01N 2030/522; G01N 2030/027; B01D 15/14; B01D 15/18; B01D 15/206; B01D 15/22; B01D 15/20; B23P 6/02
See application file for complete search history.

(56) References Cited

U.S. PATENT DOCUMENTS 4,597,866 A    7/1986 Couillard
5,021,162 A    6/1991 Sakamoto et al.
(Continued)

FOREIGN PATENT DOCUMENTS

EP    2204225 A1    7/2010
EP    3080600 A1    10/2016
(Continued)

OTHER PUBLICATIONS

Machine Translation of JP-S57158553.*
(Continued)

*Primary Examiner* — Benjamin L Lebron
(74) *Attorney, Agent, or Firm* — Eversheds Sutherland (US) LLP

(57) ABSTRACT

The invention discloses a piston for a process column, said piston comprising a top side and a bed contact side, wherein said top side comprises a drainage trench.

14 Claims, 5 Drawing Sheets

(51) Int. Cl.
*B01D 15/22* (2006.01)
*G01N 30/60* (2006.01)
*G01N 30/02* (2006.01)
*B23P 6/02* (2006.01)
*G01N 30/52* (2006.01)

(52) U.S. Cl.
CPC ............ *B23P 6/02* (2013.01); *G01N 30/6004* (2013.01); *G01N 30/6021* (2013.01); *G01N 30/6026* (2013.01); *G01N 30/6017* (2013.01); *G01N 2030/027* (2013.01); *G01N 2030/522* (2013.01)

(56) References Cited

U.S. PATENT DOCUMENTS

| | | | |
|---|---|---|---|
| 5,366,621 | A | 11/1994 | Bidell et al. |
| 5,462,659 | A | 10/1995 | Saxena et al. |
| 5,919,361 | A | 7/1999 | Moran |
| 6,019,897 | A * | 2/2000 | Horsman ............... B01D 15/14 210/101 |
| 6,280,616 | B1 | 8/2001 | Pettersson |
| 7,578,934 | B2 | 8/2009 | Gill et al. |
| 7,671,203 | B2 * | 3/2010 | Antonini ................ B01D 15/20 546/44 |
| 2006/0124525 | A1 * | 6/2006 | Bellafiore ............. B01D 15/22 210/198.2 |
| 2011/0120951 | A1 * | 5/2011 | Hampton ............. B01D 15/206 210/657 |

FOREIGN PATENT DOCUMENTS

| | | |
|---|---|---|
| JP | S5740647 A | 3/1982 |
| JP | S57158553 A | 9/1982 |
| JP | S63304161 A | 12/1988 |
| JP | 2010-151845 A | 7/2010 |
| WO | 2002/053256 A1 | 7/2002 |
| WO | 2004/103517 A1 | 12/2004 |
| WO | 2014/053872 A2 | 4/2014 |
| WO | 2015/088427 A1 | 6/2015 |

OTHER PUBLICATIONS

International Preliminary Report on Patentability Received for PCT Application No. PCT/SE2014/051463, dated Jun. 14, 2016, 5 Pages.
Extended European Search Report Received for European Patent Application No. 14870195.6, dated Jun. 9, 2017, 19 Pages.
International Search Report and Written Opinion regarding International Application No. PCT/SE2014/051463, dated Feb. 5, 2015, 12 pages.

* cited by examiner

PISTON AND PROCESS COLUMN

CROSS-REFERENCE TO RELATED APPLICATIONS

This application is a filing under 35 U.S.C. 371 of international application number PCT/SE2014/051463, filed Dec. 8, 2014, which claims priority to SE application number 1351465-8, filed Dec. 9, 2013, the entire disclosures of each of which are hereby incorporated by reference.

TECHNICAL FIELD OF THE INVENTION

The present invention relates to process columns, and more particularly to a process column with a movable piston. The invention also relates to a method of conducting maintenance on a process column.

BACKGROUND OF THE INVENTION

Figure 1:
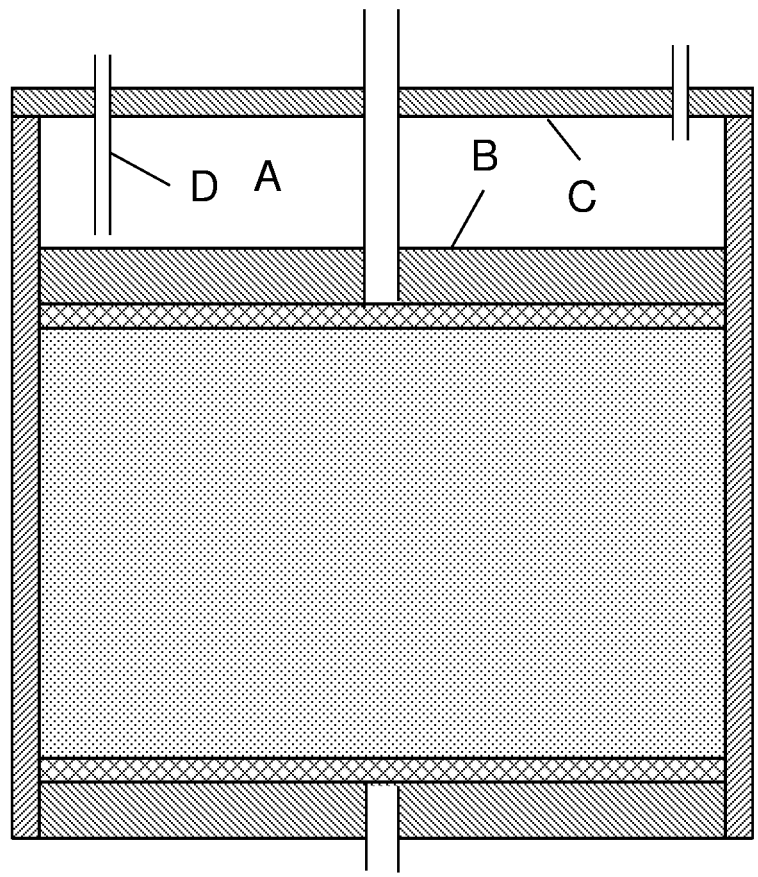

Axial columns with packed beds of particles are commonly used both in process scale chromatography and in solid-phase synthesis of e.g. peptides or oligonucleotides. In chromatography, the bed contains adsorbent particles for selectively binding and certain feed components and in solid phase synthesis the particles used have suitable reactive groups for stepwise synthesis of the peptide or oligonucleotide, In such columns, the packed particle bed is usually stabilized by compression in an axial direction using a piston (which can alternatively be called an adaptor). The compression force may be applied to the piston via e.g. a threaded rod or a hydraulic jack, but it can also be applied by the introduction of a hydraulic liquid into a hydraulic chamber A confined between the top B of the piston and a top cover C of the column, as shown in FIG. 1. This arrangement has been described in e.g. U.S. Pat. Nos. 5,021,162, 6,280,616 and WO2004/103517. Such columns are also commercially available, e.g. as FineLine or InDex columns from GE Healthcare Bio-Sciences AB (Sweden).

To avoid contamination, the hydraulic liquid is usually selected to be identical to or similar to the liquids applied to the bed in the chromatographic separation process/solid phase synthesis. In chromatography this can mean a wide range of liquids, from water (usually with 20% ethanol added as a preservative) to alcohols, acetonitrile etc, while in solid phase synthesis, acetonitrile and toluene are commonly used. Many of these liquids are both toxic and flammable, so it is highly desirable to contain them in closed systems and to avoid spillage and the formation of explosive vapour-air mixtures.

After finishing a separation campaign on a chromatography column and after finishing a synthesis on a synthesis column, the column is normally disassembled in order to remove the packed bed, clean the column and to introduce a new packed bed. In order to do this, the hydraulic fluid first has to be removed from the hydraulic chamber. Typically this is done by introducing a drainage tube D in the chamber and pumping out the liquid, e.g. by using a peristaltic pump. A significant amount of liquid will however remain in the chamber, which poses a health and explosion hazard when the column is disassembled.

Removal of liquid can also be an issue in columns which do not have a top cover above the piston. Spillage of buffers and other liquids onto the top of the column is common in process settings and these need to be removed for safety, hygiene and/or corrosion prevention reasons. On large columns, which can be up to 2 m or more in diameter, it is difficult to remove all liquid from the piston.

Accordingly there is a need for pistons, columns and methods that allow complete or essentially complete removal of liquid from the hydraulic chamber and/or the piston top side and particularly without causing exposure to vapours.

SUMMARY OF THE INVENTION

One aspect of the invention is to provide a piston for a process column where liquids such as hydraulic fluid can be conveniently and safely removed. This is achieved with a piston as defined in claim 1.

One advantage is that substantially all the liquid can be removed. A further advantage is that it can be removed under conditions where risks of accidental exposure or explosions can be avoided.

A second aspect of the invention is to provide a process column allowing convenient and safe removal of liquids, including hydraulic fluids. This is achieved with a column as defined in the claims.

One advantage is that substantially all the liquid can be removed. A further advantage is that it can be removed under conditions where risks of accidental exposure or explosions can be avoided.

Another aspect of the invention is to provide a convenient and safe method for removal of hydraulic liquid from a process column. This is achieved with a method as defined in the claims.

Further suitable embodiments of the invention are described in the dependent claims.

Definitions

It should be understood by those skilled in the art that the use of directional terms such as above, below, upper, lower, upward, downward, top, bottom and the like are used in relation to the illustrative embodiments as they are depicted in the figures, the upward direction being toward the top of the corresponding figure and the downward direction being toward the bottom of the corresponding figure.

The use of the terms "inlet" and "outlet" does not exclude the possibility of reverse flow direction, i.e. that a flow enters the column via the outlet and exits via the inlet.

DRAWINGS

Figure 2:
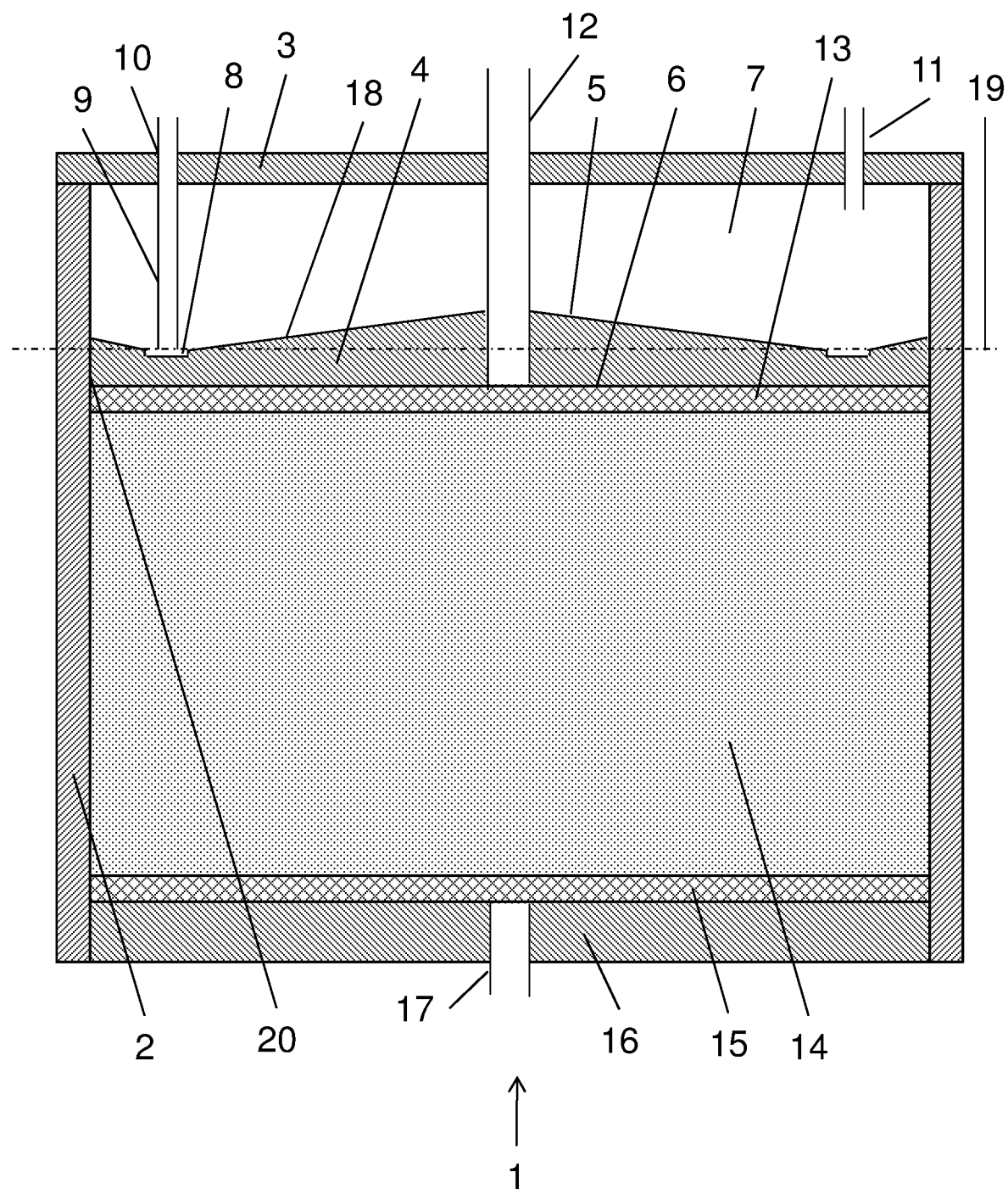
Figure 3:
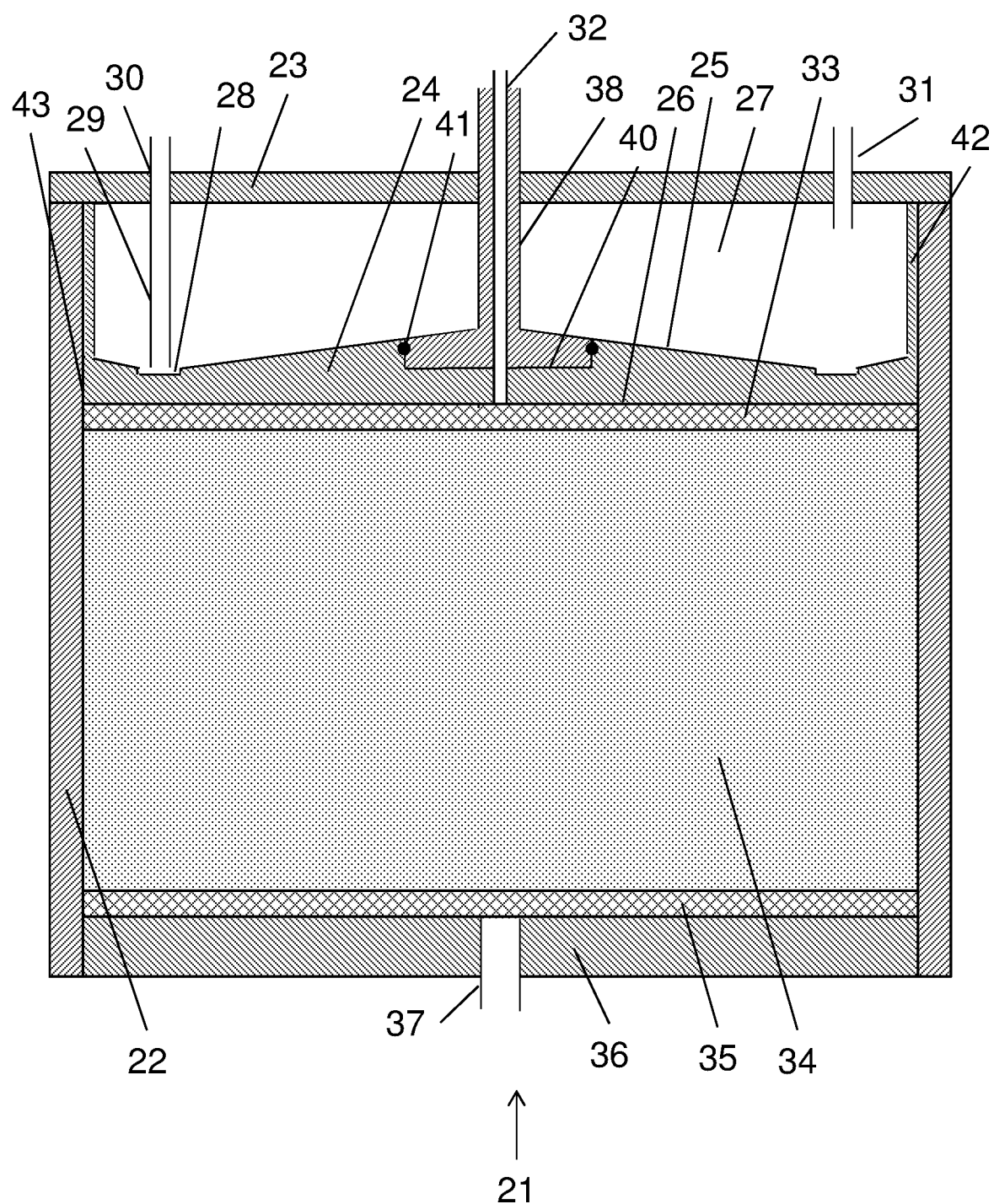
Figure 4:
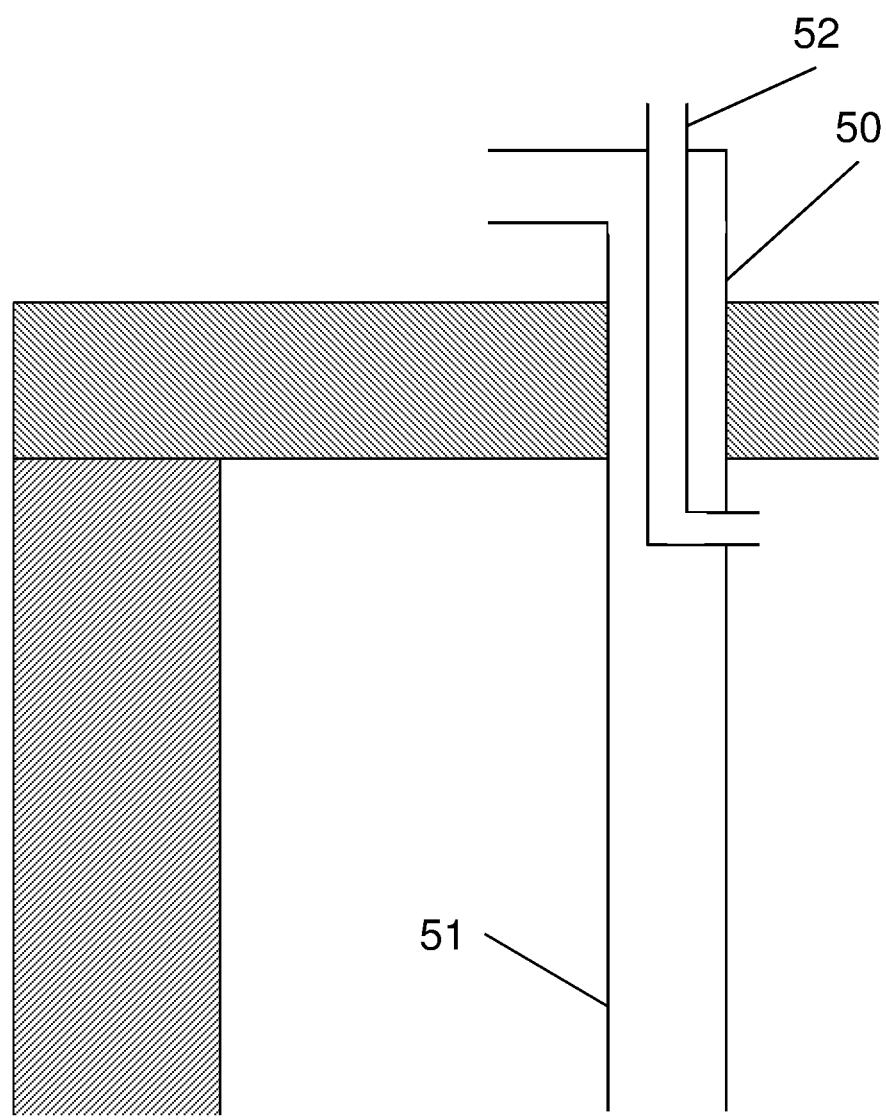
Figure 5:
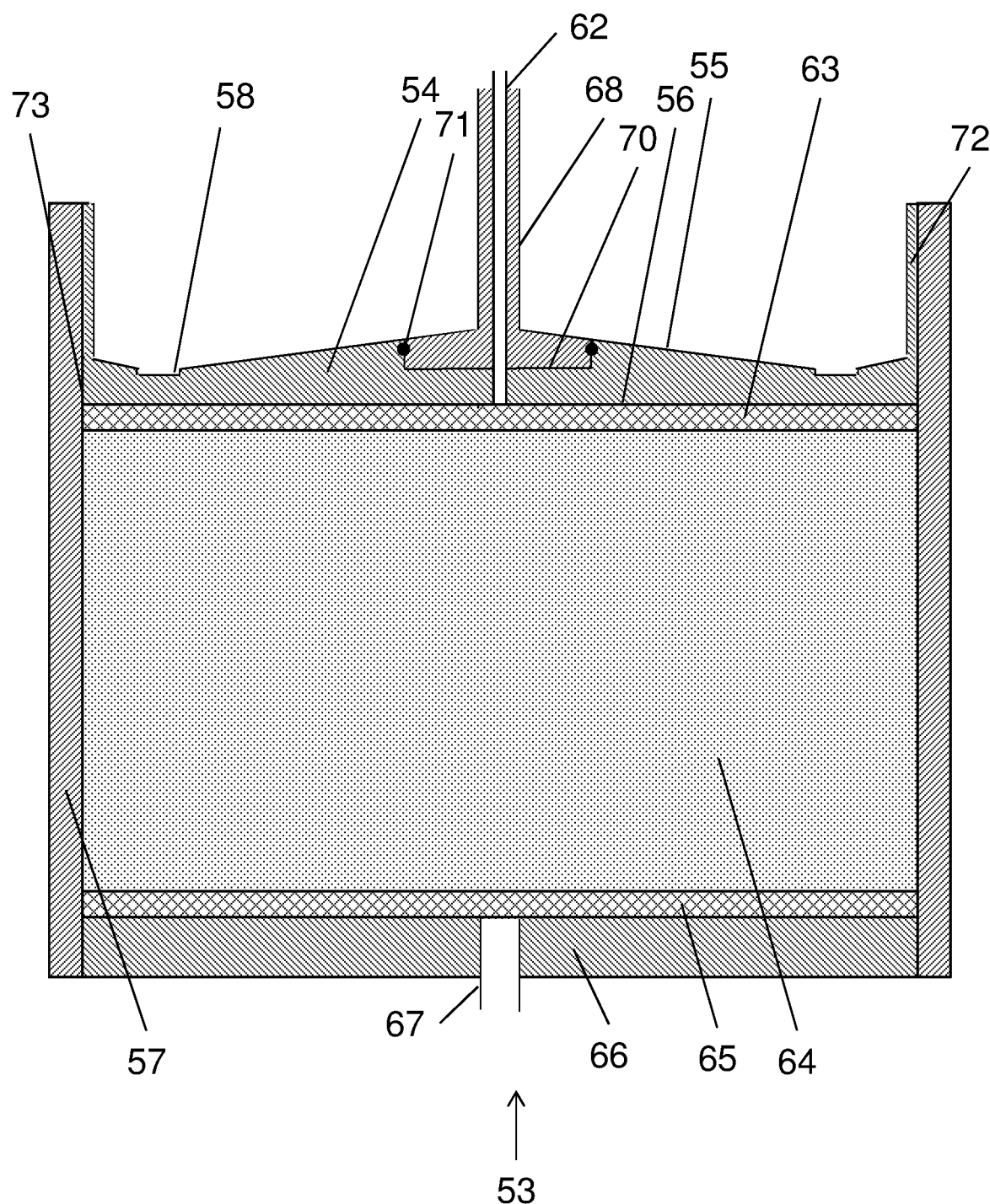

FIG. 1 shows a typical prior art column.
FIG. 2 shows a piston and a column of the invention.
FIG. 3 shows an alternative embodiment of a piston and a column of the invention.
FIG. 4 shows an arrangement with a first port, a drainage tube and a gas port for an embodiment of the invention.
FIG. 5 shows a piston of the invention mounted in an open-top column of the invention.

DETAILED DESCRIPTION OF EMBODIMENTS

In one aspect, illustrated by FIGS. 2-5, the present invention discloses a piston 4;24;54 for a process column, said piston comprising a top side 5;25;55 and a bed contact side 6;26;56, wherein said top side comprises a drainage trench 8;28;58. The piston is suitably arranged to be movable inside a column tube 2;22;57 of a process column 1;21;53. The piston may e.g. have a diameter of up to 3 m, such as 0.3-3 m or 0.5-2 m. It may have one or more sealing member (not shown) arranged around a perimeter 20;43;73 to allow for sealing against the column tube. The drainage trench allows easy removal of any liquid present above the piston when it is mounted in a column. If the column tube is open above the piston, liquids such as spillage of buffers, alkali solutions and other liquids used in process chromatography can be removed e.g. by suction from the drainage trench. If the column tube is closed above the piston, e.g. with a column top cover 3;23, liquid such as hydraulic fluids can be removed by suction from the drainage trench or by pressurizing the hydraulic chamber 7;27 formed by the piston, the column tube and the top cover. In the latter case, a drainage tube 10;30 is suitably arranged in the drainage trench in order to convey the liquid out of the column.

The drainage trench can be a recess, e,g, an elongated recess, in the top side of the piston. It can e.g. be an elongated recess with a generally flat bottom surface and side walls forming straight or obtuse angles towards the bottom surface. The side walls can e.g. have a height of 1 mm-2 cm, such as 2 mm-15 mm, and the bottom surface can e.g. have a width of 1 cm-5 cm, such as 15 mm-4 cm. The trench can be located in a lowermost location on the top side. This allows for gravity flow of the remaining liquid into the trench during removal and consequently essentially complete removal via suction or a drainage tube. The top side (or at least a portion 18 of the top side) may slope downwards toward the drainage trench in order to facilitate the gravity flow. The top side or the portion of the top side can e.g. be angled by 0.1-10, such as 1-10 or 1-5, degrees relative to the horizontal plane or to a plane 19 generally parallel with the bed contact side. The bed contact side will during normal operation of the piston in a column be essentially horizontally aligned. As illustrated in FIGS. 2 and 3, different portions of the top side can slope downwards to both sides of the drainage trench. It is also contemplated that a bottom of the drainage trench is formed by the junction of two sloping top side portions. A bottom of the drainage trench may further slope downwards to a lowermost location on the top side. The drainage trench can also comprise a drainage well to which a drainage tube or suction device may be applied to further promote the removal of any remaining liquid.

In some embodiments, the piston has a circular cross section and the drainage trench is circular and concentric with the periphery 20;43;73 of the piston. This means that the piston has a rotational symmetry and that the drainage tube will thus fit into the drainage trench irrespective of the angular arrangement of the piston inside the tube.

In some embodiments, the piston comprises a stabilizing collar 42;72 extending upwards from a periphery 20;43;73 of the piston. The stabilizing collar can prevent tilting of the piston in a column tube, which may cause jamming and potential damage to the piston and/or the column tube. As the piston with the collar will form a liquid-holding trough, efficient drainage of liquid will be even more important for these embodiments.

In a second aspect, illustrated by FIGS. 2-5, the invention discloses a process column 1;21;53, which comprises a column tube 2;22;57, a piston 4;24;54 with a top side 5;25;55, a bed contact side 6;26;56 and a drainage trench 8;28;58 as described above. A fluid distributor structure 13;33;63 may be attached to the bed contact side of the piston and a fluid inlet 12;32;62 may be fluidically connected to the distributor structure and via the distributor also to the packed bed 14;34;64 contained in the column. The column may further comprise a bottom distributor 15;35;65 resting on a bed support 16;36;66 and an outlet 17;37;67 in fluidic connection with the packed bed via the bottom distributor. The inlet 12;32;62 may be arranged as an internal part of a piston rod 38;68, which may penetrate a top cover 23 through a slidable sealing arrangement (not shown in detail), but the inlet may also e.g. be a spiral coil of flexible tubing, allowing movement of the piston inside the column.

In some embodiments the piston can be moved in the column tube through introduction of hydraulic fluid in a hydraulic chamber 7;27 delimited by the column tube, a top cover 3;23 and the piston. A drainage tube 9;29;51 can then extend from a first port 10;30;50 in the top cover or an upper portion of the column tube to the drainage trench 8;28, e.g. to a position adjacent to a bottom surface of the drainage trench. The fluid can then be removed via the drainage tube, either by pumping or by application of a gas pressure to the hydraulic compartment. The hydraulic chamber can suitably be hermetically sealed to allow for pressure being applied to the piston by the hydraulic liquid, which can e.g. be introduced via a port or tube 10;11;30;31. Hermetic sealing is also advantageous if gas pressure is used to empty the hydraulic chamber. If the hydraulic chamber comprises more than one port or tube, all but one can suitably be sealed off (e.g. by closed valves) when pressure is applied.

In some embodiments, the column is arranged for emptying the hydraulic chamber by application of a gas pressure. This can e.g. be accomplished by having a second port 11, 31, where a pressurized gas (e.g. an inert gas such as nitrogen or argon) can be introduced to force the liquid out through the drainage tube. The second port can be located in the top cover, but alternatively also in a top portion of the column tube or even in the piston rod. Alternatively, the first port 50 with the drainage tube 51 may be constructed (see e.g. FIG. 4) such that it also comprises a gas port 52, through which the pressurized gas may be introduced. In both cases, the second port or the gas port may also be used for venting when the hydraulic chamber is filled with liquid.

In certain embodiments, the column comprises at least one piston rod 38;68 removably attached to the piston. As stated above, the piston rod may comprise an inlet 32;62 and it may penetrate a top cover 23 through an opening where sealing elements are arranged to allow sliding motion of the piston rod without leakage of pressurized liquid or gas. The reason for having the piston rod removable is that it facilitates transport of the column components and that the piston rod can be exchanged separately if it is damaged. The area 40;70 of contact between said piston rod and said piston can suitably be sealed off from the hydraulic chamber by a sealing member 41;71. The sealing member can e.g. be an O-ring of an elastomeric material and serves the purpose of avoiding any stagnant liquid beneath the piston rod. Such stagnant liquid can otherwise cause contamination risks, particularly if the hydraulic liquid is water, where microbial growth can occur. It can be particularly advantageous if the upper surface of the attachment moiety of the piston rod forms an extension of the sloping top surface of the piston, such that the gravity flow proceeds unhindered all the way to the drainage trench.

In a third aspect the present invention discloses a method of conducting maintenance on a process column. The method comprises the steps of:

a) providing a column as described above, wherein the hydraulic chamber is at least partially filled with a liquid;

b) drawing off the liquid from the hydraulic chamber via the drainage tube. The drawing off may e.g. be accomplished by pressurizing the hydraulic chamber with a gas, such as an inert gas, via the second port or via the gas port. This procedure avoids the need for a pump and the used liquid can be directly conveyed under safe conditions to a vessel for either waste disposal or for reuse. It is however also possible to draw off the liquid by a pump if so desired.

To eliminate the exposure to hazardous vapors, the minute amount of liquid remaining in the trench may be removed by washing, where a washing liquid (e.g. water) is introduced in the hydraulic chamber, drawn off and if needed, another aliquot of washing liquid is added and drawn off.

After completion of the drawing off and any washing steps, the top cover may be removed and the piston removed to allow access to the packed bed and the interior of the column. Depending on the construction of the column, the top cover may be removed separately by lifting or the piston and the top cover can be removed together by lifting the piston rod. In the case where the top cover is removed separately, the piston can be raised and remove by pumping liquid into the column against a closed inlet.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties as if they were individually incorporated.

The invention claimed is:

1. A process column comprising:
   a. a column tube configured to receive liquid via an inlet;
   b. a piston being disposed within the column tube and spanning the diameter of the column tube;
   wherein, the piston defines a top side and a column bed contact side with respect to the column tube;
   c. a hydraulic chamber formed on the top side by the piston, the column tube, and a top cover of the process column;
   d. a drainage trench located on a top peripheral side of the piston and within the hydraulic chamber; and
   e. a drainage tube extending from a first port in the top cover to the drainage trench, the first port also comprising a gas port;
   wherein, when the column tube is in an opened or closed position above the piston, suction from the drainage trench within the hydraulic chamber facilitates the removal of liquid from the hydraulic chamber; and
   wherein, when the column tube is in a closed position above the piston, application of pressure to the drainage trench within the hydraulic chamber facilitates the removal of liquid from the hydraulic chamber.

2. The process column of claim 1, wherein said drainage trench is located in a lowermost location on the top side.

3. The process column of claim 1, wherein at least a portion of the top side slopes downwards toward said drainage trench.

4. The process column of claim 3, wherein the portion is angled by 1-10 degrees relative to a plane generally parallel with said bed contact side.

5. The process column of claim 3, wherein the piston has a circular cross section and wherein said drainage trench is circular and concentric with a periphery of the piston.

6. The process column of claim 3, further comprising a stabilizing collar extending upwards from a periphery of the piston.

7. The process column of claim 3, wherein the piston is movable in the column tube through introduction of hydraulic fluid in the hydraulic chamber.

8. The process column of claim 1, further comprising a second port in the top cover or the column tube.

9. The process column of claim 1, further comprising at least one piston rod attached to the piston.

10. The process column of claim 9, wherein said piston rod is removably attached to said piston.

11. The column of claim 10, wherein an area of contact between the piston rod and the piston is sealed off from the hydraulic chamber by a sealing member.

12. A method of conducting maintenance on a process column, comprising the steps of:
   a) providing a column according to claim 1, wherein the hydraulic chamber is at least partially filled with liquid;
   b) drawing off the liquid from the hydraulic chamber via said drainage tube.

13. The method of claim 12, wherein step b) is performed by pressurizing the hydraulic chamber with a gas, such as an inert gas, via said second port or via the gas port.

14. The method of claim 12, further comprising a step of:
   c) removing the top cover and the piston from the column.

* * * * *